United States Patent [19]
Iijima et al.

[11] Patent Number: 5,708,494
[45] Date of Patent: Jan. 13, 1998

[54] OPHTHALMOLOGICAL INSTRUMENT

[75] Inventors: Hiroshi Iijima; Akinari Takagi, both of Tokyo, Japan

[73] Assignee: Kabushiki Kaisha Topcon, Tokyo, Japan

[21] Appl. No.: 564,569

[22] Filed: Nov. 28, 1995

[30] Foreign Application Priority Data

Nov. 29, 1994 [JP] Japan .................................. 6-294626

[51] Int. Cl.$^6$ ................................ A61B 3/14; A61B 3/10
[52] U.S. Cl. .................................... 351/208; 351/211
[58] Field of Search ................................ 351/208, 221, 351/211, 205, 200, 246; 128/648, 645

[56] References Cited

U.S. PATENT DOCUMENTS

5,107,851  4/1992  Yano et al. ........................ 128/648

Primary Examiner—Hung X. Dang
Attorney, Agent, or Firm—Finnegan, Henderson, Farabow, Garrett & Dunner, L.L.P.

[57] ABSTRACT

An ophthalmological instrument is provided in which optical members can be satisfactorily cleaned, the times for cleaning can be reduced and reliability of measuring accuracy can be improved. An alignment between a cornea (C) of an eye (E) to be tested and an instrument body is detected by projecting an alignment detecting light toward the cornea (C) through alignment detecting optical systems (30, 40) and receiving a luminous flux reflected on the cornea (C) through a light receiving sensor (45). A working distance between the cornea (C) and the instrument body is detected projecting a working distance detecting light toward the cornea (C) through working distance detecting optical systems (50, 60) and receiving a luminous flux reflected on the cornea (C) by a light receiving sensor (63). Part of optical paths of the alignment detecting optical systems (30, 40) and the working distance detecting optical systems (50, 60) are not used in common. Dirt stuck to optical members arranged in part of the optical paths which are used in common is detected in accordance with signals from the light receiving sensors (45, 63).

8 Claims, 6 Drawing Sheets

OPHTHALMOLOGICAL INSTRUMENT

BACKGROUND OF THE INVENTION

1. Field of the Invention

This invention relates to an ophthalmological instrument capable of detecting dirt adhering to optical members.

2. Description of the Prior Art

Heretofore, there is known an ophthalmolgical instrument, such as a non-contact type tonometer, in which a target spot light is projected by an objective lens such that the spot light is imaged on the center of curvature of an eye to be tested, a reflected light of the projected light by specular reflection on a cornea of the eye is received by light receiving means again through the objective lens, alignment between the cornea and an instrument body is carried out based on clearness and position of the target spot image formed on the light receiving means, an air pulse is injected toward the cornea from an injection nozzle to alter the shape of the cornea when the adjustments of the alignment and working distance are completed, and parallel rays of light are projected toward the flattened cornea, and then the reflected light is received by the light receiving means, thereby calculating an intraocular pressure.

However, in such an ophthalmological instrument, cases occur in which tears etc. scattered when the air pulse is injected to the cornea adhere to optical members located before the eye. If such stuck tears should be left as they are, they would become dirt or stains as a cause of reduced quantity of light, or the like. Since this makes it difficult to obtain an accurate result of measurement, optical members are frequently subjected to cleaning irrespective of dirt on the optical members.

SUMMARY OF THE INVENTION

It is, therefore, an object of the present invention to provide an ophthalmological instrument in which optical members can correctly be cleaned, times of cleaning can be reduced, and reliability with respect to the measuring accuracy can be improved.

In order to achieve the above object, according to one aspect of the present invention, there is provided an ophthalmological instrument comprising an alignment detecting optical system for detecting an alignment between a cornea of an eye to be tested and an instrument body by projecting an alignment detecting light toward the cornea and receiving a luminous flux reflected on the cornea by first light receiving means and a working distance detecting optical system for detecting a working distance between the cornea and the instrument body by projecting a working distance detecting light toward the cornea and receiving a luminous flux reflected on the cornea by second light receiving means. Part of optical paths of the alignment detecting optical system and the working distance detecting optical system is not subjected to common use. Dirt on optical members arranged in that part of the optical paths which are not subjected to common use is detected in accordance with signals from the first and second light receiving means.

According to another aspect of the present invention, there is provided an ophthalmological instrument comprising an alignment detecting optical system for detecting an alignment between a cornea of an eye to be tested and an instrument body by projecting an alignment detecting light toward the cornea and receiving a luminous flux reflected on the cornea by first light receiving means, a working distance detecting optical system for detecting a working distance between the cornea and the instrument body by projecting a working distance detecting light toward the cornea and receiving a luminous flux reflected on the cornea by second light receiving means, and a cornea transfiguration detecting optical system for detecting transfiguration of the cornea by projecting a cornea transfiguration detecting light toward the cornea and receiving a luminous flux reflected on the cornea by third light receiving means. At least part of optical paths of at least one of the alignment detecting optical system and the working distance detecting optical system and an optical path of the cornea transfiguration detecting optical system is not subjected to common use. Dirt on optical members arranged in that part of the optical paths which are not subjected to common use is detected in accordance with a signal from the first or second light receiving means and a signal from the third light receiving means.

According to still another aspect of the present invention, there is provided an ophthalmological instrument comprising an eye position detecting optical system for detecting an alignment and a working distance between a cornea of an eye to be tested and an instrument body by projecting alignment and working distance detecting light toward the cornea and receiving a luminous flux reflected on the cornea by light receiving means, and a cornea transfiguration detecting optical system for detecting transfiguration of the cornea by projecting a cornea transfiguration detecting light toward the cornea and receiving a luminous flux reflected on the cornea by light receiving means. At least part optical paths of the eye position detecting optical system and the cornea transfiguration detecting optical system is not subjected to common use. Dirt on optical members arranged in that part of the optical paths which are not subjected to common use is detected in accordance with signals from the light receiving means of the optical systems.

According to still another aspect of the present invention, there is provided an ophthalmological instrument comprising an eye position detecting optical system for detecting an alignment and a working distance between a cornea of an eye to be tested and an instrument body by projecting alignment and working distance detecting light toward the cornea and receiving a luminous flux reflected on the cornea by light receiving means, and a cornea transfiguration detecting optical system for detecting transfiguration of the cornea by projecting a cornea transfiguration detecting light toward the cornea and receiving a luminous flux reflected on the cornea by light receiving means. Dirt on optical members arranged in position where passage areas of respective luminous fluxes of the corneal transfiguration detecting optical system and the eye position detecting optical system are different is detected in accordance with signals from the respective light receiving means of the respective optical systems.

In a construction of the present invention as recited above, an alignment between the cornea and the instrument body is detected by projecting an alignment detecting light toward the cornea of the eye by the alignment detecting optical system and receiving the luminous flux reflected on the cornea by the first light receiving means. A working distance between the cornea and the instrument body is detected by projecting a working distance detecting light toward the cornea by the working distance detecting optical system which does not commonly use a part of the optical path of the alignment detecting optical system and receiving the luminous flux reflected on the cornea by the second light receiving means. The dirt on the optical members arranged in the optical path, which is not commonly used, is detected in accordance with a signals from the first and second light receiving means.

Further, in a construction of the present invention as recited above, an alignment between the cornea and the instrument body is detected by projecting an alignment detecting light toward the cornea of the eye by the alignment detecting optical system and receiving the luminous flux reflected on the cornea by the first light receiving means, a distance between the cornea and the instrument body is detected by projecting a working distance detecting light toward the cornea by the working distance detecting optical system and receiving the luminous flux reflected on the cornea by the second light receiving means, a cornea transfiguration is detected by projecting a cornea transfiguration detecting light toward the cornea by the cornea transfiguration detecting optical system which does not commonly use at least a part of the optical path of at least one of the alignment detecting optical system and the working distance detecting optical system and receiving the luminous flux reflected on the cornea by the third light receiving means, and the dirt on the optical members arranged in the optical path, which is not commonly used, is detected in accordance with the signal from the first or second light receiving means and the signal from the third light receiving element.

Further, in a construction of the present invention as recited above, an alignment and a working distance between the cornea and the instrument body are detected by projecting a detecting light for alignment and working distance detection toward the cornea by the eye position detecting optical system and receiving the luminous flux reflected on the cornea by the light receiving means, a cornea transfiguration is detected by projecting a cornea transfiguration detecting light toward the cornea by the cornea detecting optical system which does not commonly use at least a part of the optical path of the eye position detecting optical system and receiving the luminous flux reflected on the cornea by the light receiving means, and the dirt on the optical members arranged in the optical path, which is not commonly used, is detected in accordance with the signals from the respective light receiving means.

Further, in a construction of the present invention as recited above, an alignment and a working distance between the cornea and the instrument body are detected by projecting a detecting light for alignment and working distance detection toward the cornea by the eye position detecting optical system and receiving the luminous flux reflected on the cornea by the light receiving means, a cornea transfiguration is detected by projecting a cornea transfiguration detecting optical light toward the cornea by the cornea transfiguration detecting optical system and receiving the luminous flux reflected on the cornea by the light receiving means, and the dirt on the optical members arranged in position where the areas of passage of the respective luminous fluxes of the cornea transfiguration detecting optical system and the eye position detecting optical system are different is detected in accordance with signals from the respective light receiving means.

According to still another aspect of the present invention, there is provided a non-contact type tonometer comprising an anterior portion observing optical system for observing an eye to be tested, an injection nozzle arranged in coaxial relation with an optical axis of the anterior portion observing optical system and adapted to inject an air pulse toward the cornea via an optical member facing the eye, an alignment detecting optical system for aligning an instrument body with respect to the eye in up and down, and left and right directions, and a working distance detecting optical system for detecting a working distance of the instrument body with respect to the eye. The alignment detecting optical system includes an alignment detecting optical system for projecting an alignment detecting light to the cornea through the injection nozzle, and an alignment receiving optical system for receiving light reflected on the cornea. The working distance detecting optical system includes a working distance detecting light projecting optical system for projecting a working distance detecting light towards the cornea across the optical member, and a working distance detecting light receiving optical system for receiving the working distance detecting light-reflected on the cornea.

According to still another aspect of the present invention, there is provided a non-contact type tonometer comprising an anterior portion observing optical system for observing an eye to be tested, an injection nozzle arranged in coaxial relation with an optical axis of the anterior portion observing optical system and adapted to inject an air pulse toward the cornea via an optical member facing the eye, and an alignment detecting optical system for aligning an instrument body with respect to the eye in up and down, and left and right directions. The alignment detecting optical system includes an alignment detection light projecting optical system for projecting an alignment detecting light to the cornea through the injection nozzle, and an alignment receiving optical system lot receiving light reflected on the cornea.

DETAILED DESCRIPTION OF THE PREFERRED EMBODIMENT (Embodiment 1)

Figure 1:
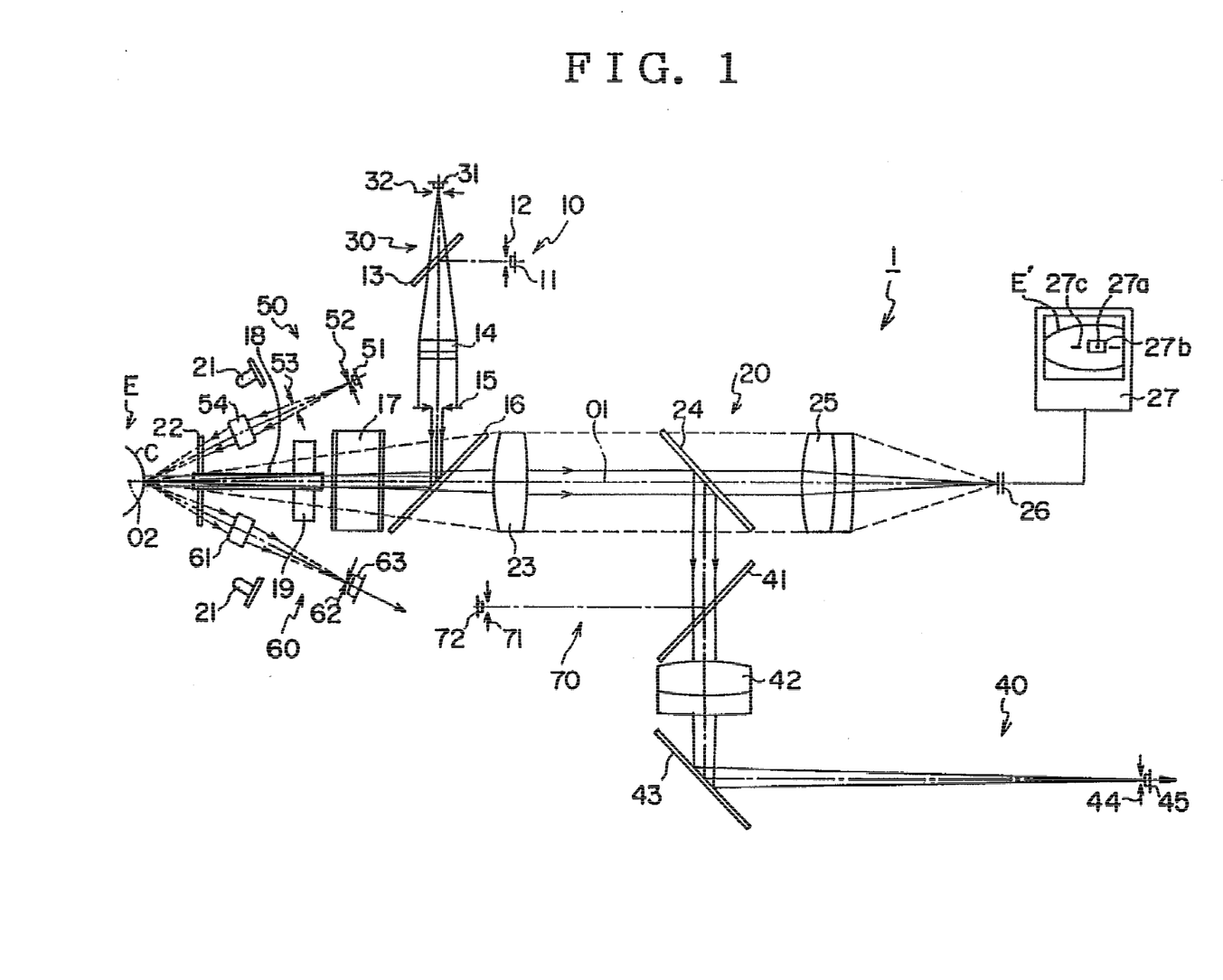
FIG. 1 shows an ophthalmological instrument according to the present invention and is an explanatory view of optical systems in which alignment and working distance adjustments have been made.
Figure 2:
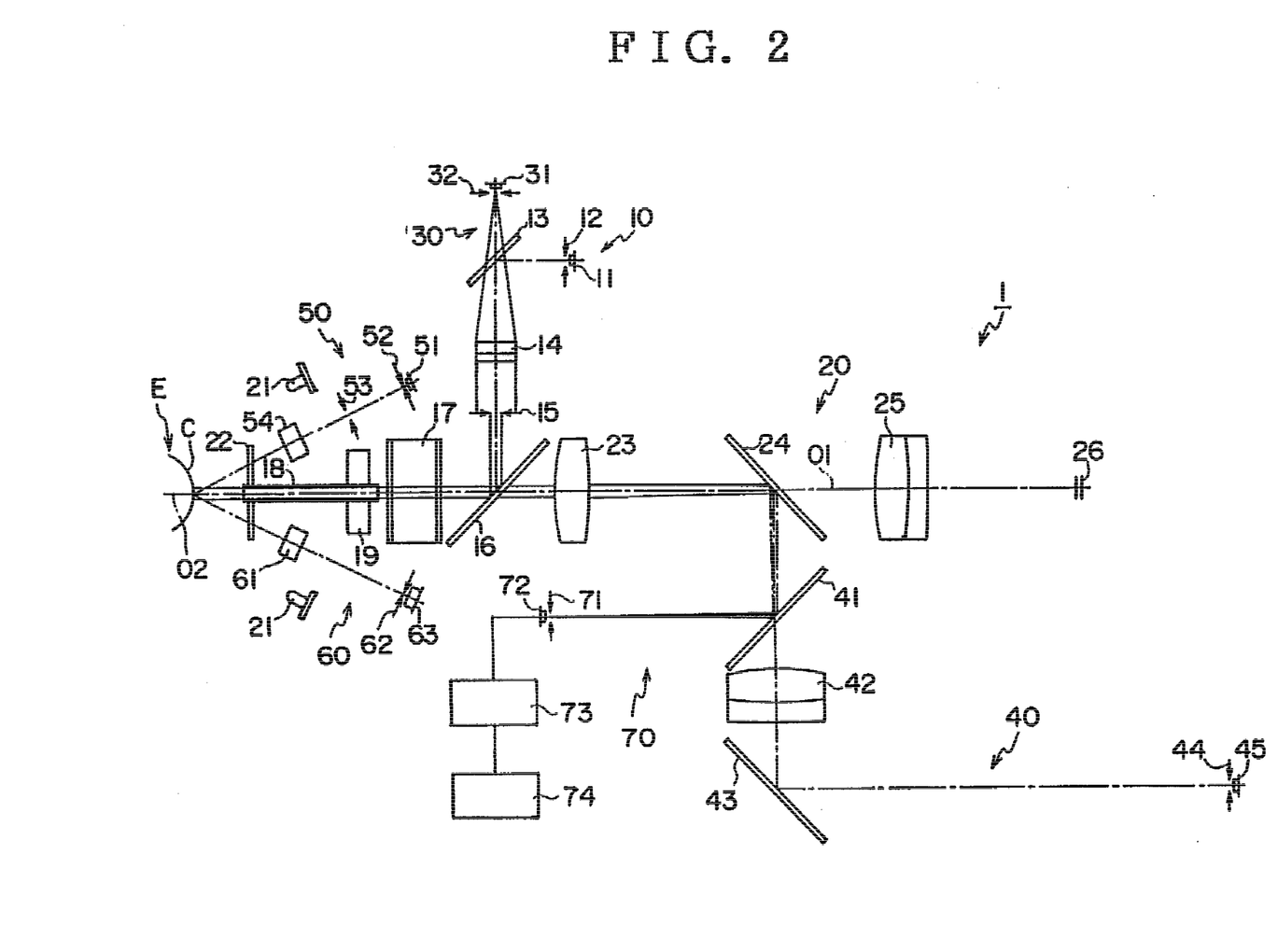
FIG. 2 is likewise an explanatory view of optical systems in which a transfigured (flattened) cornea of an eye to be tested is being detected.

FIGS. 1 and 2 show a First embodiment of an ophthalmological instrument of the present invention. Specifically, FIG. 1 is an explanatory view of an optical system in which the adjustments of an alignment and a working distance have been made, and FIG. 2 is an explanatory view of the optical system in which the detection of a transfigured (flattened) cornea is being undergone.

In FIGS. 1 and 2, an ophthalmological instrument 1 comprises a fixation mark projecting optical system 10 for projecting a gazing mark for sight fixation to an eye E to be tested in order to guide the sight of the eye E, an anterior portion observing optical system 20 for observing an image of an anterior portion including the eye E, an alignment light projecting optical system 30 for projecting an alignment light to the eye E, an alignment light receiving optical system 40 for receiving an alignment light reflected on a cornea C of the eye E, a working distance detecting light projecting optical system 50 for projecting a working distance detecting light to the eye E, a working distance detecting light receiving optical system 60 For receiving a working distance detecting light reflected on the cornea C, and a cornea transfiguration detecting optical system 70 for optically detecting the transfiguration, if any, of the cornea C.

The fixation mark projecting optical system 10 includes an LED 11 for emitting a visible light, an aperture diaphragm 12, a wavelength division filter 13 for reflecting a visible light and allowing a near infrared light to pass therethrough, a collimator lens 14, a diaphragm 15, a half mirror 16, a chamber window glass 17, and an injection nozzle 18.

The injection nozzle 18 is supported by a transparent support plate 19. The chamber window glass 17 and the transparent support plate 19 are of a frame structure for surrounding a supplying device (not shown) for supplying an air pulse to the injection nozzle A visible light emitted by the LED 11 is allowed to pass through the aperture diaphragm 12 located in focusing position of the collimator lens 14, reflected by the wavelength division filter 13, converted into parallel rays of light by the collimator lens 14, reduced into a reduced image by the diaphragm 15, then reflected by the half mirror 16, allowed to pass through the chamber window glass 17, and then through the injection nozzle 18 to provide a reduced image on the cornea C of the eye E. A patient is requested to fixedly gaze at the gazing mark as this reduced image so that the sight is guided toward the gazing mark and fixed thereon.

The anterior portion of observing optical system 20 includes an LED 21 for emitting an infrared light for directly illuminating the eye E from left and right, a fixed cover glass 22 attached to a distal end of the injection nozzle 18, transparent support plate 19, the chamber window glass 17, the half mirror 16, an objective lens 23, a half mirror 24, an imaging lens 25, and a CCD camera 26.

The objective lens 23 is set such that it allows luminous fluxes emitted respectively by the LED 21 and another LED 31 (later described) and reflected by the cornea C to pass therethrough, whereas a visible light emitted from the LED 11 and reflected by the cornea C so that the visible light is not introduced to optical members arranged after the objective lens 23.

An infrared light emitted by the LED 21 and reflected by the eye E is, as shown in FIG. 1, allowed to pass through the fixed cover glass 22, the transparent support plate 19, the chamber window glass 17 and the half mirror 16, converted into parallel rays of light by the objective lens 23, further allowed to pass through the half mirror 24 and then gathered by the imaging lens 25 so as to form an image in the CCD camera 26.

The image formed in the CCD camera 26 is converted into a digital signal by a control circuit and a picture signal processing Circuit (both not shown) and displayed on a monitor 27 as an anterior portion image E'.

The alignment light projecting optical system 30 includes an LED 31, an aperture diaphragm 32, the wavelength division filter 13, the collimator lens 14, the diaphragm 15, the half mirror 16, the chamber window glass 17, and the injection nozzle 18.

Each of those optical members of the alignment light projecting optical system 30 from the LED 31 to the injection nozzle 18 also acts as a detecting light projecting optical system for projecting a cornea transfiguration detecting light toward the cornea C in order to optically detect the transfiguration of the cornea C by injecting an air pulse from the injection nozzle 18 to the cornea C.

The near infrared light which has been emitted by the LED 31 and has passed the aperture diaphragm 32 is allowed to pass through the wavelength division filter 13, converted into parallel rays of light by the collimator lens 14, reduced into a reduced image by the diaphragm 15, then reflected by the half mirror 16, further allowed to pass through the chamber window glass 17, and then through the injection nozzle 18 to provide a reduced image on the cornea C of the eye E, and then reflected by the cornea C.

The alignment light imaging optical system 40 includes the injection nozzle 18, the chamber window glass 17, the half mirror 16, the objective lens 23, the half mirror 24, a half mirror 41, an imaging lens 42, a total reflecting mirror 43, a diaphragm 44, and a light receiving sensor 45.

The alignment luminous flux emitted by the LED 31 and reflected by the cornea C is allowed to pass through the injection nozzle 18 and then through the chamber window glass 17 and the half mirror 16, converted into parallel rays of light by the objective lens 23, and guided to the half mirror 24.

Part of the parallel rays of light guided to the half mirror 24 are allowed to pass through the half mirror 24 and further guided to the CCD camera 26 so that it is displayed on the monitor 27, as an alignment target image 27a, together with the anterior portion image E'. An alignment allowable range mark 27b is electrically or optically projected to the monitor 27 so that a working distance detecting bar 27c (for example, the bar becomes shorter as the working distance is more correctly adjusted), which is expanded and contracted based on information from a working distance detecting optical system 60 (later described), is displayed on the monitor 27.

The other part of the parallel rays of light guided to the half mirror 24 are reflected by the half mirror 24, allowed to pass through the half mirror 41, guided to the imaging lens 42, collected by the imaging lens 42, reflected by the total reflecting mirror 43, imaged on the diaphragm 44, and then made incident on the light receiving sensor 45.

The alignment light projecting optical system 30 and the alignment light imaging optical system 40 act as an alignment detecting optical system for detecting an aligning state between a visual line 02 of the eye E and an optical axis 01 in accordance with a signal from the light receiving sensor 45.

The working distance detecting light projecting optical system 50 includes an infrared LED 51, a pin hole plate 52, an aperture 53, an objective lens 54, and the fixed cover glass 22. The aperture 53 is located in a front focusing position of the objective lens 54.

The infrared light emitted by the infrared LED 51 is allowed to pass through the pin hole plate 52 forming a target image, further allowed to pass through the aperture 53, collected by the objective lens 54, further allowed to pass through the fixed cover glass 22, and projected to the vertex of the cornea C.

The working distance detecting optical system 60 includes the fixed cover glass 22, an imaging an 61, a pin hole plate 62, and a light receiving sensor 63.

The working distance detecting light reflected by the vertex of the cornea C is allowed to pass through the fixed cover glass 22, collected by the imaging lens 61 guided to the pin hole plate 62 to pass therethrough, and then guided to the light receiving sensor 63.

In this way, the working distance detecting light projecting optical system 50 and the working distance detecting optical system 60, which are arranged in symmetrical relation with reference to the optical axis 01, act as a working distance detecting optical system for detecting a working distance from the vertex of the cornea C to the distal end of the injection nozzle 18 in accordance with a signal from the light receiving sensor 63.

A cornea transfiguration detecting optical system 70 includes the injection nozzle 18, the chamber window glass 17, the half mirror 16, the objective lens 23, the half mirrors 24, 41, a diaphragm 71, and a light receiving sensor 72.

It should be noted that a known cornea transfiguration air pulse supplying device, not shown, is employed. In this known device, a piston is reciprocally moved within a cylinder in response to the driving of a rotary solenoid, an air pulse is injected toward the cornea C when the piston is shifted to one side, and the vertex of the cornea C is transfigured by the injected air pulse. In the course of the transfiguration, a transfigured anterior portion is displayed on the monitor 27 by the anterior portion observing optical system 20.

The cornea transfiguration detecting luminous flux (parallel rays of light) reflected by the transfigured cornea C is, as shown in FIG. 2, allowed to pass through the injection nozzle 18, further through the chamber window glass 17 and the half mirror 16, then through the objective lens 23, reflected by the half mirrors 24, 41, imaged on the diaphragm 71, and made incident on the light receiving sensor 72.

Since the quantity of light received by the light receiving sensor 72 is increased as soon as the transfiguration of the cornea C is started, the intraocular pressure is measured by known procedures, in accordance with a signal indicative of increasing quantity of light received by the light receiving sensor 72 due to transfiguration of the cornea C.

Figure 3:
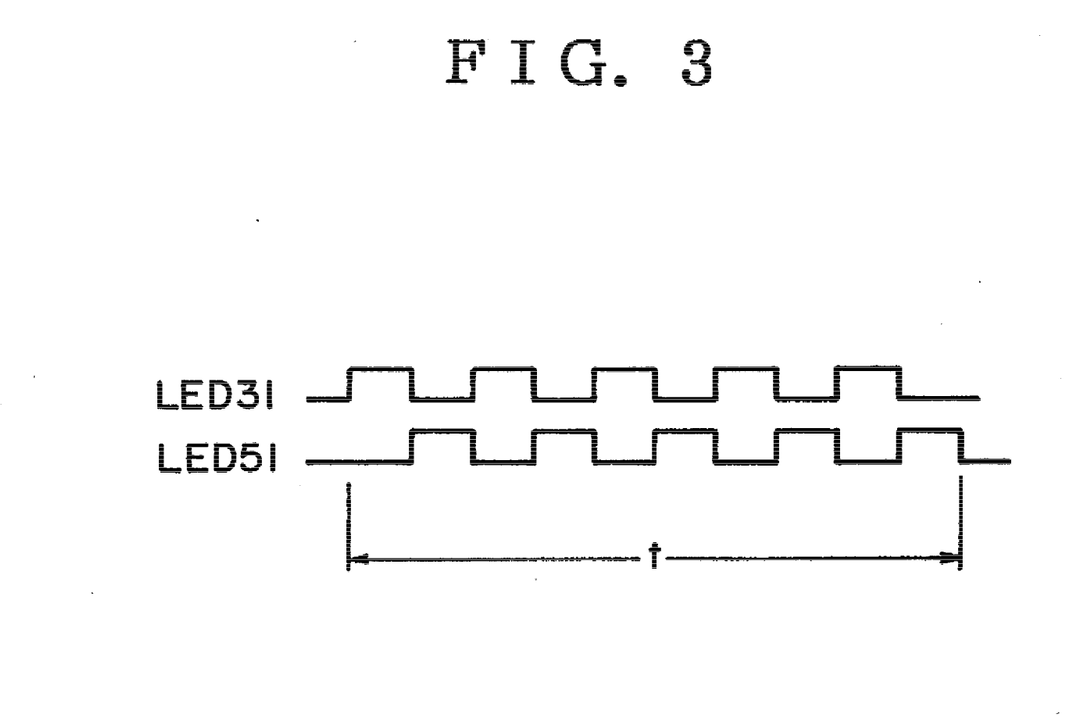
FIG. 3 is likewise an explanatory view in which outgoing pulses of two LEDs are compared.

On the other hand, the LEDs 31, 51 are driven by respective LED driving circuits which are controlled by a control arithmetic Unit, not shown. The LEDs 31, 51 are turned on and off alternately as shown in FIG. 3.

Figure 4:
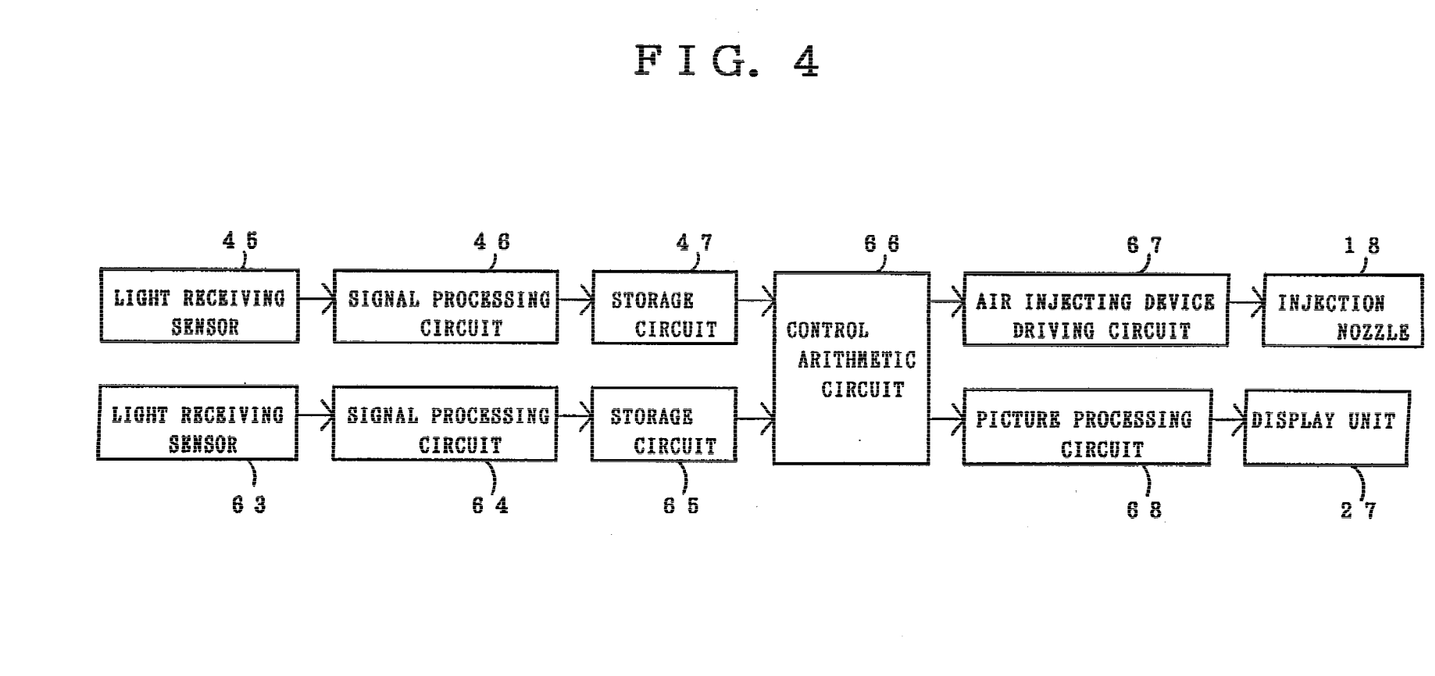
FIG. 4 is a block diagram showing a control system for detecting dirt, employed in the ophthalmological instrument according to the present invention.

An output from the light receiving sensor 45 is, as shown in FIG. 4, input into a signal processing circuit 46 which detects the output from the light receiving sensor 45 so that the output is stored in a storage circuit 47, when the LED 31 is in the ON-state. On the other hand, an output from the light receiving sensor 63 is input into a signal processing circuit 64 which detects the output from the light receiving sensor 63 so that the output is stored in a storage circuit 65, when the LED 51 is in the ON-state.

Detected data of the storage circuits 47, 65 are input into the control arithmetic unit 68, so that when the detected data of the storage circuits 47, 65 are a predetermined value or more for a predetermined time t (see FIG. 3), in other words, when it is judged that the alignment and the working distance are correct and, therefore, the eye E is in a proper allowable range, a signal is sent to an air injecting device driving circuit 67 and an air is injected toward the cornea C from the injection nozzle 18.

At the same time, the arithmetic unit 66 calculates the sum total of the detected data of the storage circuit 47 and the sum total of the detected data of the storage circuit 65 for the time t, Also, the ratio of each sum total is calculated and compared with the data of the comparator indicating a predetermined ratio. If the sum total of the detected data of the storage circuit 65 is judged as lower than a reference ratio with reference to the sum total of the detected data of the storage circuit 47 as a result of this comparison, a signal is sent to an LED driving circuit so that a current value of the LED 51 is automatically controlled to be increased to become the reference ratio. However, in case the current value of the LED 51 is brought to be maximum or goes beyond the maximum value as a result of the control, a signal is sent to a picture processing circuit 88 and thereby a warning sentence demanding a cleaning of the fixed cover glass 22 is employed on the monitor 27.

In this way, since the fixed cover glass 22, which is likely to be soiled by dirt due to tears directly scattered from the eye E, is not present in an optical path of the alignment light projecting optical system 30 nor in an optical path of the alignment light imaging optical system 40 but it is present only in an optical path of the working distance detecting light projecting optical system 50 and in an optical path of the working distance detecting optical system 60, the dirt on the fixed cover glass 22 affects only the quantity of light made incident on the light receiving sensor 63 and it does not effect the quantity of light made incident on the light receiving sensor 45. Accordingly, the dirt on the fixed cover glass 22 can correctly be detected by the aforementioned comparison.

In the above example, although the ratio of the sum total of the detected data of the storage circuits 47, 65 for the predetermined time t is utilized, the ratio of the detected data of the storage circuits 47, 65 after the passage of the predetermined time t may be employed. In the alternative, the ratio of the maximum values of the detected data of the storage circuits 47, 65 for the predetermined time t may be employed.

Figure 5:
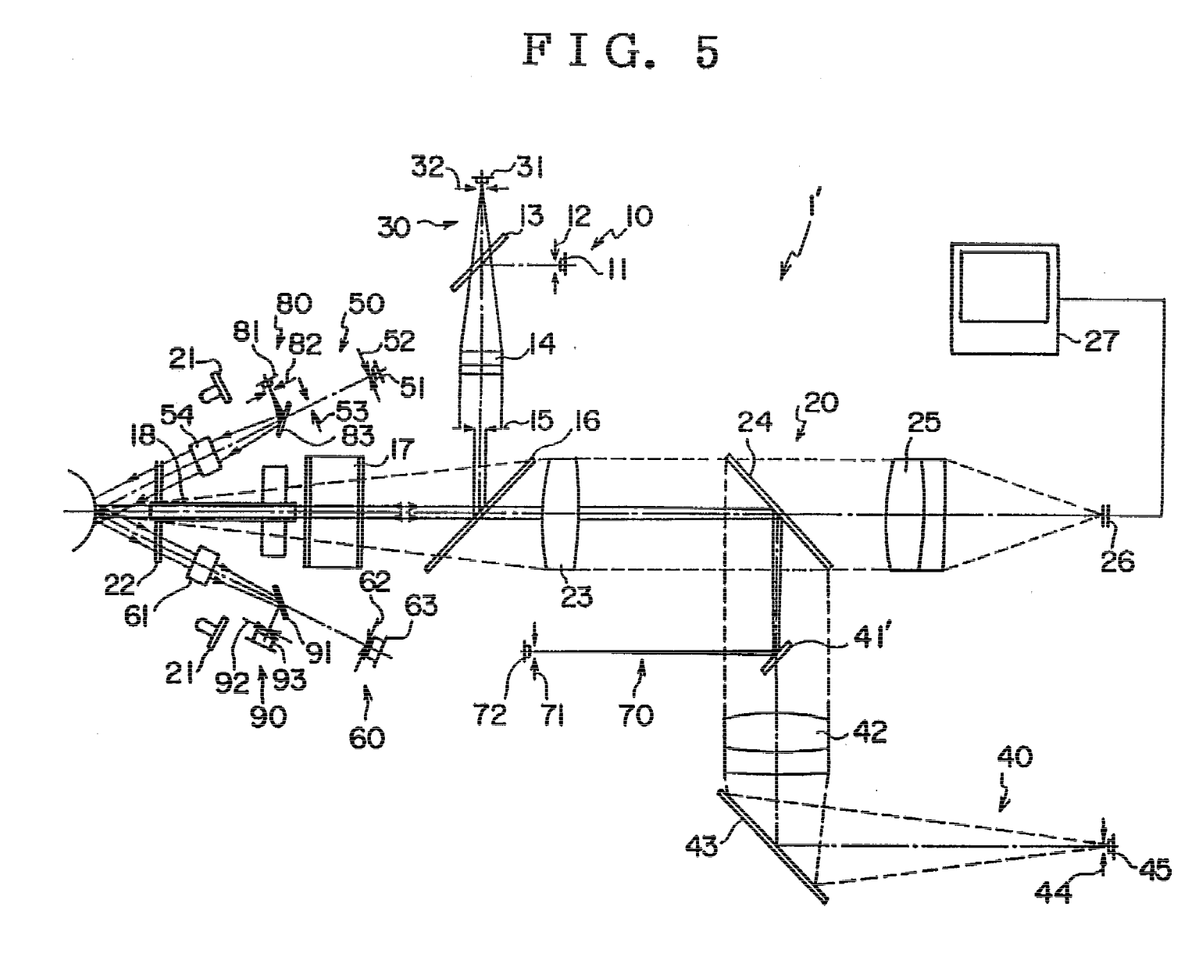
FIG. 5 shows a second embodiment of an ophthalmological instrument according to the present invention and is an explanatory view of optical systems in which a transfigured cornea of an eye to be tested is being detected.

FIG. 5 shows a second embodiment of the present invention in which a transfigured (or flattened) cornea C is shown. In FIG. 5, the luminous flux indicated by broken lines represents a luminous flux reflected by the cornea C of the alignment light projecting optical system, showing a state in which alignment is being adjusted before the cornea C is transfigured. Its substantial operation is the same as that in the first embodiment. The same construction as that of the first embodiment is denoted by the same reference numeral and description thereof is omitted.

In FIG. 5, an ophthalmological instrument 1' comprises a fixation mark projecting optical system 10, an anterior portion observing optical system 20, an alignment light projecting optical system 30, an alignment light receiving optical system 40, a working distance detecting light projecting optical system 50, a working distance detecting light receiving optical system 60, a cornea transfiguration detecting optical system 70, a second cornea transfiguration detecting light projecting optical system 80 for detecting the transfiguration (or flatness) of the cornea C, and a second cornea transfiguration detecting optical system 90.

The second comes transfiguration detecting light projecting optical system 80 includes an infrared LED 81, a pin hole plate 82 disposed in a front focusing position of the objective lens 54, an aperture 53, a half mirror 83 disposed between an aperture 53 and an objective lens 54 and adapted to reflect a luminous flux coming from the pin hole plate 82 toward the cornea C, the objective lens 54, and a cover glass 22.

A cornea transfiguration detecting light emitted by the infrared LED 81 illuminates the pin hole plate 82. The luminous flux, which has passed through the pin hole plate 82, is reflected by the half mirror 83, converted into parallel rays of light by the objective lens 54, and allowed to pass through the cover glass 22 to illuminated the cornea C.

The second cornea transfiguration detecting optical system 90 includes the cover glass 22, an imaging lens 61, a half mirror 91 disposed between the imaging lens 61 and the pin hole plate 62, a pin hole plate 92, and a light receiving sensor 93.

The luminous flux reflected on the flattened cornea C is allowed to pass through the cover glass 22, collected by the imaging lens 61, reflected by the half mirror 91 further allowed to pass through the pin hole plate 92, and guided to the light receiving sensor 93.

The intraocular pressure is obtained by a known technique based on an air pressure injected from the air injecting device when the light quantity of the light received by the receiving sensor 93 becomes a maximum, or when the light quantity of the light received by the receiving sensor 72 becomes a maximum, or when both of the light quantities of light received by the sensors 93, 72 become maximum.

The maximum light quantities of the light receiving sensors 93, 72 at that time are stored in respective storage circuits through the signal processing circuit. Based on the data, the ratio of the quantities of light received by the light receiving sensor 93 and 72 is calculated by the control arithmetic unit. In case the light quantity received by the light receiving sensor 93 is lower than the predetermined allowable range with respect to the predetermined ratio, a warning sentence demanding the cleaning of the fixed cover glass 22 is displayed on the monitor 27 and attention is demanded by buzzer or the like.

In this way, since the fixed cover glass 22, which is likely to be soiled with dirt due to tears directly scattered from the eye E, is not present in the optical path of the cornea transfiguration detecting optical system 70 but it is present only in the optical path of the working distance detecting light projecting optical system 50 and in the optical path of the working distance detecting optical system 60, the dirt on the fixed cover glass 22 affects the quantity of light made incident on the light receiving sensor 93 and it does not affect the quantity of light made incident on the light receiving sensor 72. Accordingly, the dirt on the fixed cover glass 22 can correctly be detected by the afore-mentioned comparison.

In the above example, although the light quantity is detected by a combination of the pin hole plate 92 and the light receiving sensor 93, the light position detecting sensor may be located in the position where the detecting pin hole plate 92 is located (the remaining construction is also the same). The half mirror 41 of the alignment detecting optical system 40 may be a total reflection mirror 41' which is located only in a central portion of the optical path.

Figure 6:
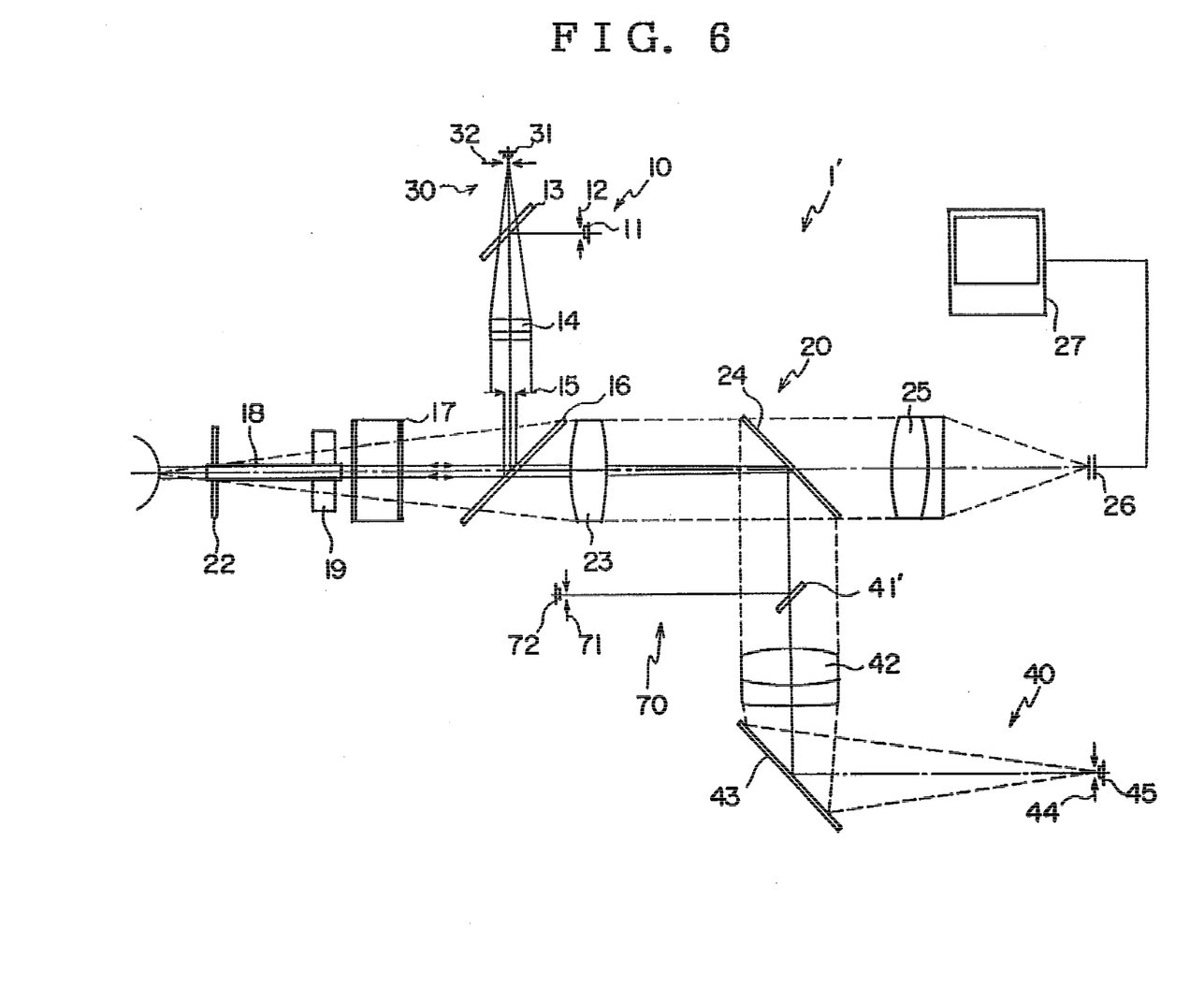
FIG. 6 shows a third embodiment of an ophthalmological instrument according to the present invention and is an explanatory view of optical systems in which a transfigured cornea is being detected.

FIG. 6 shows a third embodiment of the present invention in which a transfigured (flattened) cornea C is shown. In FIG. 6, the luminous flux indicated by broken lines represents a luminous flux reflected on the cornea C, showing a state in which alignment is being adjusted before the cornea C is transfigured. The construction of the third embodiment is the same as that of the second embodiment except that the alignment light projecting optical system 30 also serves as a working distance detecting light projecting optical system, and the alignment light receiving optical system 40 also serves as a working distance detecting light receiving optical system. In this embodiment, the detections of the alignment and the working distance are carried out based on the level of the light quantity of the light received by receiving sensor 45.

If a state where the level of the light quantity of the light received by receiving sensor 45 is equal to or more than a predetermined value, that is, if a state where the alignment and the working distance are within s predetermined allowable range continuously for the predetermined time t, the air pulse supplying device is actuated to inject an air pulse from the injection nozzle 18 and, as a result, the cornea C is transfigured (flattened). At the same time, the maximum light quantity level of the light received by receiving sensor 45 is stored for this predetermined time t.

On the other hand, the quantity of light received by the light receiving sensor 72 is increased as soon as the transfiguration of the cornea C is started and the intraocular pressure is obtained by a known technique. The maximum light quantity level of the light received by receiving sensor 72 at that time is stored.

The control arithmetic unit calculates the ratio between the stored maximum light quantity level of the light received by receiving sensor 45 and the maximum light quantity level of the light received by receiving sensor 72 and compares the result with a predetermined ratio.

As a result of this comparison, when it is found that the stored maximum light quantity level of the light received by receiving sensor 72 is equal to or more than the predetermined value and the maximum light quantity level of the light received by receiving sensor 45 is lowered an allowable range with respect to the maximum light quantity level of the light received by receiving sensor 72, it is detected as dirt being present en the cover glass 22 and this fact is displayed outside.

The above arrangement is made so that the cover glass 22, which is likely to be soiled with dirt due to tears directly scattered from the eye E is disposed only in the optical path of the alignment light receiving optical system 40, and the dirt on the cover glass 22 affects only the light quantity made incident on the light receiving sensor 45 but it does not affect the light quantity made incident on the light receiving sensor 72.

On the other hand, as a result of the above comparison, when the stored maximum light quantity level of the light received by receiving sensor 45 is equal to or more than the predetermined value and the maximum light quantity level of the light received by receiving sensor 72 is lower than an allowable range with respect to the maximum light quantity level of the light receiving sensor 45, it is detected as dirt being present on the cover glass 22 and this fact is displayed outside. This arrangement is made so that the tears directly scattered from the eye E is taken through the injection nozzle 18 and only the dirt in the vicinity of the optical axis adheres to the chamber window glass 17, and so that this dirt affects only the light quantity level of the light received by receiving sensor 72, but it hardly affects the light quantity made incident on the light receiving sensor 45.

That is, on the chamber window glass 17, the area of passage of the luminous flux made incident on the light receiving sensor 72 is a narrow area in the vicinity of the central portion where the dirt is stuck, whereas the area of passage of the luminous flux made incident on the light receiving sensor 45 is a wide area of the periphery excluding the central portion. Accordingly, the dirt on the chamber window glass 17 substantially causes only the lowering of the level of the light quantity of the light received by receiving sensor 72.

In this way, by means of comparison of the level of the stored maximum light quantity of the light received by sensor 45 with the level of the stored maximum light quantity of the light received by receiving sensor 72, the dirts on the cover glass 22 and on chamber window glass 17 can correctly be detected.

An ophthalmological instrument according to the present invention comprises an alignment detecting optical system for detecting an alignment between the cornea and the instrument body by projecting an alignment detecting light toward a cornea of an eye to be tested and receiving a luminous flux reflected by the cornea by first light receiving means, and a working distance detecting optical system for detecting a working distance between the cornea and the instrument body by projecting a working distance detecting light toward the cornea and receiving the luminous flux reflected by the cornea by second light receiving means, part of optical paths of the alignment detecting optical system and the working distance detecting optical system being not subjected to common use, dirt on optical members arranged in that part of the optical paths which are not subjected to common use being detected in accordance with signals from the first and second light receiving means. Owing to this arrangement, optical members can correctly be cleaned, times of cleaning can be reduced, and reliability with respect to the measuring accuracy can be improved.

What is claimed is:

1. An ophthalmological instrument comprising:

an alignment detecting optical system for detecting an alignment between a cornea of an eye to be tested and an instrument body by projecting an alignment detecting light toward the cornea and receiving a luminous flux reflected by the cornea by first light receiving means; and a working distance detecting optical system for detecting a working distance between the cornea and the instrument body by projecting a working distance detecting light toward the cornea and receiving a luminous flux reflected by the cornea by second light receiving means;

wherein part of optical paths of said alignment detecting optical system and said working distance detecting optical system is not subjected to common use, and dirt stuck on optical members arranged in said part of said optical paths which are not subjected to common use is detected in accordance with signals from said first and second light receiving means.

2. An ophthalmological instrument comprising:

an alignment detecting optical system for detecting an alignment between a cornea of an eye to be tested and an instrument body by projecting an alignment detecting light toward the cornea and receiving a luminous flux reflected by the cornea by first light receiving means;

a working distance detecting optical system for detecting a working distance between the cornea and the instrument body by projecting a working distance detecting light toward the cornea and receiving a luminous flux reflected by the cornea by second light receiving means; and a cornea transfiguration detecting optical system for detecting transfiguration of the cornea by projecting a cornea transfiguration detecting light toward the cornea and receiving a luminous flux reflected on the cornea by third light receiving means;

wherein at least one part of optical paths of at least one of said alignment detecting optical system and said working distance detecting optical system and at least one part of an optical path of said cornea transfiguration detecting optical system are not subjected to common use, and dirt stuck on optical members arranged in said part of said optical paths which are not subjected to common use is detected in accordance with a signal from said first or second light receiving means and a signal from said third light receiving means.

3. An ophthalmological instrument comprising;

an eye position detecting optical system for detecting an alignment and a working distance between a cornea of an eye to be tested and an instrument body by projecting alignment and working distance detecting light toward the cornea and receiving a luminous flux reflected by the cornea by light receiving means; and a cornea transfiguration detecting optical system for detecting transfiguration of the cornea by projecting a cornea transfiguration detecting light toward the cornea and receiving a luminous flux reflected by the cornea by light receiving means;

wherein at least one part of optical paths of said eye position detecting optical system and said cornea transfiguration detecting optical system is not subjected to common use, and dirt on optical members arranged in said part of said optical paths which are not subjected to common use is detected in accordance with signals from said respective light receiving means of said optical systems.

4. An ophthalmological instrument comprising:

an eye position detecting optical system for detecting an alignment and a working distance between a cornea of an eye to be tested and an instrument body by projecting alignment and working distance detecting light toward the cornea and receiving a luminous flux reflected by the cornea by light receiving means; and a cornea transfiguration detecting optical system for detecting transfiguration of the cornea by projecting a cornea transfiguration detecting light toward the cornea and receiving a luminous flux reflected by the cornea by light receiving means;

wherein dirt on optical members arranged in position where passage areas of respective luminous fluxes of said corneal transfiguration detecting optical system and said eye position detecting optical system are different from each other is detected in accordance with signals from said respective light receiving means of said optical systems.

5. A non-contact type tonometer comprising:

an anterior portion observing optical system for observing an eye to be tested;

an injection nozzle arranged in coaxial relation with an optical axis of said anterior portion observing optical system and adapted to inject an air pulse toward the cornea via an optical member facing the eye;

an alignment detecting optical system for aligning an instrument body with respect to the eye in up and down, and left and right directions; and a working distance detecting optical system for detecting a working distance of the instrument body with respect to the eye;

said alignment detecting optical system including an alignment detection light projecting optical system for projecting an alignment detection light to the cornea through said injection nozzle, and an alignment detection light receiving optical system for receiving the alignment detection light reflected by the cornea;

said working distance detecting optical system including a working distance detection light projecting optical system for projecting a working distance detection light toward the cornea across said optical member, and a working distance detection light receiving optical system for receiving the working distance detection light reflected by the cornea.

6. A non-contact type tonometer according to claim 5, wherein said optical member is a cover glass.

7. A non-contact type tonometer according to claim 5, wherein the alignment detection light traveling within said injection nozzle toward the eye are parallel rays of light.

8. A non-contact type tonometer according to claim 5, wherein said alignment detection light receiving optical system receives the alignment detection light reflected by the cornea through said injection nozzle.

* * * * *